US006455251B1

(12) United States Patent
Waldman

(10) Patent No.: US 6,455,251 B1
(45) Date of Patent: *Sep. 24, 2002

(54) METHODS OF AND KITS AND COMPOSITIONS FOR DIAGNOSING COLORECTAL TUMORS AND METASTASIS THEREOF

(75) Inventor: Scott A. Waldman, Ardmore, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/304,193

(22) Filed: May 3, 1999

Related U.S. Application Data

(63) Continuation of application No. 09/046,178, filed on Mar. 23, 1998, now Pat. No. 5,928,873, which is a continuation of application No. 08/789,270, filed on Jan. 28, 1997, now Pat. No. 5,731,159, which is a continuation of application No. 08/305,056, filed on Sep. 13, 1994, now Pat. No. 5,601,990.

(51) Int. Cl.$^7$ ................................................. C12Q 1/68

(52) U.S. Cl. ................................ 435/6; 436/63; 436/64

(58) Field of Search ........................ 435/4, 6; 436/63, 436/64

(56) References Cited

U.S. PATENT DOCUMENTS

| | | | |
|---|---|---|---|
| 4,584,268 A | 4/1986 | Ceriani et al. |
| 4,683,195 A | 7/1987 | Mullis et al. |
| 4,683,202 A | 7/1987 | Mullis et al. |
| 4,965,188 A | 10/1990 | Mullis et al. |
| 5,075,216 A | 12/1991 | Innis et al. |
| 5,160,723 A | 11/1992 | Welt et al. |
| 5,237,051 A | 8/1993 | Garbers et al. |
| 5,518,888 A | 5/1996 | Waldman |
| 5,601,990 A | 2/1997 | Waldman |
| 5,731,159 A | 3/1998 | Waldman |

FOREIGN PATENT DOCUMENTS

ZA            839512            12/1983

OTHER PUBLICATIONS

Almenoff et al., "Ligand–based Histochemical Localization and Capture of Cells Expressing Heat–Stable Enterotoxin Receptors", *Mol. Microb.*, 1993, 8, 865–873.
Bjorn et al., "Antibody–Pseudomonas Exotoxin A Conjugates Cytotoxic to Human Breast Cancer Cells In Vitro", *Cancer Research*, 1986, 46, 3262–3267.
Bjorn et al., "Evaluation of Monoclonal Antibodies for the Development of Breast Cancer Immunotoxins", *Cancer Research*, 1985, 45, 1214–1221.
Bodansky et al., "Peptide Synthesis", John Wiley and Sons, 2d Ed., (1976).
Burgess et al., "Biological Evaluation of a Methanol–Soluble, Heat–Stable *Escherichia coli* Enterotoxin in Infant Mice, Pigs, Rabbits and Calves", *Infect. Immun.*, 1978, 21, 526–531.
Cawley et al., "Epidermal Growth Factor–Toxin A Chain Conjugates: EGF–Ricin A is a Potent Toxin While EGF–Diphtheria Fragment A is Nontoxic", *Cell*, 1980, 22, 563–570.
Ceriani, R. et al., "Variability in Surface Antigen Expression of Human Breast Epithelial Cells Cultured from Normal Breast, Normal Tissue Peripheral to Breast Carcinomas, and Breast Carcinomas", *Cancer Res.*, Jul., 1984, 44, 3033–3039.
Ceriani, R. et al., "Circulating Human Mammary Epithelial Antigens in Breast Cancer", *PNAS USA*, 1982, 79, 5420–5424.
Chan et al., "Amino Acid Sequence of Heat–stable Enterotoxin Produced by *Escherichia coli* Pathogenic for Man", *J. Biol. Chem.*, 1981, 256, 7744–7746.
Chung et al., "Enzymatically Active Peptide from the Adenosine Dithosphate–Ribosylating Toxin of *Pseudomonas aeruginosa*", 1977, 16, 832–841.
Cohen, M. et al., "Receptors for *Escherichia coli* Heat Stable Enterotoxin in Human Intestine and in a Human Intestinal Cell Line (Caco–2)", *J. Cell. Physiol.*, 1993, 156, 138–144.
Corstens, F. et al. "Chemotactic peptides: New Locomotion for Imaging of Infection?", *J. Nucl. Med.*, 1991, 32(3), 491–494.
Cumber et al., "Preparation of Antibody–Toxin Conjugates", *Meth. Enzymol.*, 1985, 112, 207–225.
Currie et al., "Guanylin: An endogenous Activator of Intestinal Guanylate Cyclase", *Proc. Natl. Acad. Sci. USA*, 1992, 89, 947–951.
de Sauvage, F. et al., "Primary Structure and Functional Expression of the Human Receptor for *Escherichia coli* Heat–stable Enterotoxin", *J. Biol. Chem.*, 1991, 266, 17912–17918.
Dreyfus et al., "Chemical Properties of Heat–Stable Enterotoxins Produced by Interotoxigenic *Escherichia coli* of Different Host Origins", *Infect. Immun.*, 1983, 42, 539–548.

(List continued on next page.)

*Primary Examiner*—Sheela Huff
(74) *Attorney, Agent, or Firm*—Woodcock Washburn LLP

(57) ABSTRACT

In vitro methods of determining whether or not an individual has metastasized colorectal cancer cells are disclosed. In vitro methods of determining whether or not tumor cells are colorectal in origin are disclosed. In vitro kits for practicing the methods of the invention and to reagents and compositions useful to practice the methods, for example as components in such in vitro kits of the invention are provided. Methods of and kits and compositions for analyzing tissue samples from the colon tissue to evaluate the extent of metastasis of colorectal tumor cells are disclosed.

4 Claims, No Drawings

OTHER PUBLICATIONS

Drewett, J. et al., "The Family of Guanylyl Cyclase Receptors and Their Ligands", *Endocrine Reviews*, 1994, 15(2), 135–162.

Eckelman et al., "Comparison of $^{99m}$Tc and $^{111}$In Labeling of Conjugated Antibodies", *Nucl. Med. Biol.*, 1986, 13, 335–343.

Evans et al., "Difference in the Response of Rabbit Small Intestine to Heat–Labile and Heat–Stable Enterotoxins of *Escherichia coli*", *Infect. Immun.*, 1973, 7, 873–880.

Fischman, Alan J. et al., "A Ticket to Ride: Peptide Radiopharmaceuticals", *J. Nucl. Med.*, 1993, 34(12), 2253–2263.

Fitzgerald et al., "Adenovirus–Induced Release of Epidermal Growth Factor and pseudomonas Toxin into the Cytosol of KB Cells during Receptor–Mediated Endocytosis", *Cell*, 1983, 32, 607–617.

Fitzgerald et al., "Construction of Immunotoxins Using Pseudomonas Exotoxin A", *Methods in Enzymology*, 1987, 151, 139–145.

Forte, L. et al., "Receptors and cGMP Signaling Mechanism for *E. coli* Enterotoxin in Opossum Kidney", *Am. J. Physiol.*, 1988, 255 (5 Pt. 2), F1040–F1046.

Forte, L. et al., "*Escherichia coli* Enterotoxin Receptors: Localization in Opossum Kidney, Instestine, and Testis", *Am. J. Physiol.*, 1989, 257 (Pt. 2), F874–881.

Forte, L. et al., "Guanylin: A Peptide Regulator of Epithelial Transport", *FASEB J*, 1995, 9, 643–650.

Giannella et al., "Development of a Radioimmunoassay for *Escherichia coli* Heat–Stable Enterotoxin: Comparison with the Suckling mouse Bioassay", *Infection and Immunity*, 1981, 33, 186–192.

Gros, O. et al., "Biochemical Aspects of Immunotoxin Preparation", *J. Immunol. Meth.*, 1985, 81, 283–297.

Guarino, A. et al., "T$^{84}$ Cell Receptor Binding and Guanyl Cyclase Activation by *Escherichia coli* Heat–Stable Toxin", *Am. J. Physiol*, 253 (Gastrointest. Liver Physiol. 16): G775–780, 1987.

Guerrant, R. et al., "Activation of Intestinal Guanylate Cyclase by Heat–Stable Enterotoxin of *Escherichia coli*: Studies of tissue Specificity, Potential Receptors, and Intermediates", *J. Infect. Dis.*, 1980, 142(2), 220–228.

Gyles, G.L., "Discussion Heat–Labile and Heat–Stable Forms of the Enterotoxin from *E. coli* Strains Enteropathogenic for Pigs", *Ann. N.Y. Acad. Sci.*, 1979, 16, 314–321.

Hakki et al., "Solubilization and Characterization of Functionally Coupled *Escherichia coli* Heat–Stable Toxin Receptors and Particulate Guanylate Cyclase Associated with the Cytoskeleton Compartment of Intestinal Membranes", *Int. J. Biochem.*, 1993, 25, 557–566.

Hardingham, J.E. et al., "Immunobead–PCR: A Technique for the Detection of Circulating Tumor Cells Using Immunomagnetic Beads and the Polymerase Chain Reaction", *Cancer Research*, 1993, 53, 3455–3458.

Hugues et al., "Identification and Characterization of a New Family of High–Affinity Receptors for *Escherichia coli* Heat–Stable Enterotoxin in Rat Intestinal Membranes", *Biochemistry*, 1991, 30, 10738–10745.

Humm, J.L., "Dosimetric Aspects of Radiolabeled Antibodies for Tumor Therapy", *J. Nuclear Med.*, 1986, 27, 1490–1497.

Klipstein et al., "Development of a Vaccine of Cross–Linked Heat–Stable and Heat–Labile Enterotoxins that Protects Against *Escherichia coli* Producing Either Enterotoxin", *Infect. Immun.*, 1982, 37, 550–557.

Krause, W. et al., "Autoradiographic Demonstration of Specific Binding Sites for *E. coli* Enterotoxin in Various Epithelia of the North American Oppossum", *Cell Tissue Res.*, 1990, 260, 387–394.

Krejcarek et al., "Covalent Attachment of Chelating Groups to Macromolecules", *Biochem. Biophys. Res. Commun.*, 1977, 77, 581–585.

Kwok et al., "Calculation of Radiation Doses for Nonuniformity Distributed $\beta$ and $\gamma$ Radionuclides in Soft Tissue", *Med. Phys.*, 1985, 12, 405–412.

Leonard et al., "Kinetics of Protein Synthesis Inactivation in Human T–Lymphocytes by Selective Monoclonal Antibody–Ricin Conjugates", *Cancer Res.*, 1985, 45, 5263–5269.

Lima, A. et al., "The Effects of *Escherichia coli* Heat–Stable Enterotoxin in Renal Sodium Tubular Transport", *Pharmacology & Toxicology*, 1992, 70, 163–167.

Magerstaedt, M. et al. "Antibody Conjugates and Malignant Disease", CRC Press, Boca Raton, 1991, 42–45 and 110–152.

Masuho et al., "Importance of the Antigen–Binding Valency and the Nature of the Cross–Linking Bond in Ricin A–Chain Conjugates with Antibody", *J. Biochem.*, 1982, 91, 1583–1591.

Merrifield, "Solid Phase Peptide Synthesis. I. The Synthesis of a Tetrapeptide", *J. Am. Chem., Soc.*, 1963, 85, 2149–2154.

Michel et al., "Fluorescence Studies of Nucleotides Binding to Diphtheria Toxin and Its Fragment A", *Biochim. et Biophys. Acta*, 1974, 365, 15–27.

Moseley et al., "Isolation and Nucleotide Sequence Determination of a Gene Encoding a Heat–Stable Enterotoxin of *Escherichia coli*", *Infect. Immunity*, 1983, 39, 1167–1174.

Okamoto et al., "Substitutions of Cysteine Residues of *Escherichia coli* Heat–Stable Enterotoxin By Oligonucleotide–Directed Mutagenesis", *Infect. Immunity*, 1987, 55, 2121–2125.

Rao, M. et al., "Mode of Action of Heat–Stable *Escherichia coli* Enterotoxin Tissue and Subcellular specificities and Role of Cyclic GMP", *Biochim. et Biophys. Acta*, 1980, 632, 35–46.

Richardson, T.C., "Astatine ($^{211}$At) as a Therapeutic Radionuclide. The Plasma: Blood Cell Distribution in Vitro", *Nucl. Med. Biol.*, 1986, 13, 583–584.

Sack, "Human Diarrheal Disease Caused by Enterotoxigenic *Escherichia coli*", *Ann. Rev. Microbiol.*, 1975, 29, 333–353.

Schulz, S. et al., "Cloning and Expression of Guanylin", *J. Biol. Chem.*, 1992, 267(23), 16019–16021.

Shimonishi et al., "Mode of Disulfide Bond Formation of a Heat–Stable Enterotoxin (ST$_h$) Produced by a Human Strain of Enterotoxigenic *Escherichia coli*", *FEBS Letters*, 1987, 215, 165–170.

So et al., "Nucleotide Sequence of the Bacterial Thansposon Tn1681 Encoding a Heat–Stable (ST) Toxin and Its Identification in Enterotoxigenic *Escherichia coli* Strains", *Proc. Natl. Acad. Sci. USA*, 1980, 77, 4011–4015.

Spitler et al., "Therapy of Patients with Malignant Melanoma Using a Monoclonal Antimelanoma Antibody–Ricin A Chain Immunotoxin", *Cancer Research*, 1987, 47, 1717–1723.

Steinstraβer et al., "Selection of Nuclides for Immunoscintigraphy/Immunotherapy", *J. Nucl. Med.*, 1988, 29(5), 875.

Thompson et al., "Biological and Immunological Characteristics of $^{125}$I–4Tyr and—18Tyr *Escherichia coli* Heat–Stable Enterotoxin Species Purified by High–Performance Liquid Chromatography", *Analytical Biochemistry*, 1985, 148, 26–36.

Thompson, M.R., "*Escherichia coli* Heat–Stable Enterotoxins and Their Receptors", *Pathol. Immunopathol. Res.*, 1987, 6, 103–116.

Thorpe, et al., "New Coupling Agents for the Synthesis of Immunotoxins Containing a Hindered Disulfide Bond with Improved Stability In Vitro", *Cancer Research*, 1987, 47, 5924–5931.

Vaandrager, A. et al., "Atriopeptins and *Escherichia coli* Enterotoxin ST$^a$ Have Different Sites of Action in Mammalian Intestine", *Gastroenterology*, 1992, 102(4), 1161–1169.

Waldman and O'Hanley, "Influence of a Glycine or Proline Substitution on the Functional Properties of a 14–Amino–Acid Analog of *Escherichia coli* Heat–Stable Enterotoxin", *Infection and Immunity*, 1989, 57, 2420–2424.

Wessels and Rogus, "Radionuclide Selection and Model Absorbed Dose Calculations for Radiolabeled Tumor Associated Antibodies", *Med. Phys.* 1984, 11, 638–645.

White, A. et al., "Opossum Kidney Contains a Functional Receptor for the *Escherichia coli* Heat–Stable Enterotoxin", *Biochemical Biophysical Res. Comm.*, 1989, 159(1), 363–367.

Worrell et al., "Effect of Linkage Variation on Pharmacokinetics of Ricin A Chain–Antibody Conjugates in Normal Rats", *Anti–Cancer Drug Design*, 1986, 1, 179–188.

Yoshimura et al., "Essential Structure for Full Interotoxigenic Activity of Heat–Stable Enterotoxin Produced by Enterotoxigenic *Escherichia coli*", *FEBS Lett.*, 1985, 181, 138–142.

Franz et al., "The Production of $^{99m}$Tc–Labeled Conjugated Antibodies Using A Cyclam–Based Bifunctional Chelating Agent", *Nucl. Med. Biol.*, 1987, 14, 569–572.

Bailey's Textbook of Histology, 16 Edition, Coperhaven, et al., Williams and Wilkens, Baltimore, MD, p. 404 (1975).

Wide, "Solid Phase Antigen–Antibody Systems", Radioimmunoassay Methods, Kirkham, Ed., E & S pp. 405–412, Livingstone, Edinburgh, (1971).

Vaandrager, A. et al., *J. Biol. Chem.*, Jan. 25, 1993, 268(3), 2174–2179 (Abstract Only).

Aitken, R. et al., "Recombinant enterotoxins as vaccines against *Escherichia coli*–mediated diarrhoea", *Vaccine*, 1993, 11(2), 227–233.

Chelly, J. et al., "Ilegitimate transcription: Transcription of any gene in any cell type", *Proc. Natl. Acad. Sci. USA*, 1989, 86, 2617–2621.

Chelly, J. et al., "Illegitimate Transcription: Application to the Analysis of Truncated Transcripts of the Dystrophin Gene in Nonmuscle Cultured Cells from Duchenne and Becker Patients", *J. Clin. Invest.*, 1991, 88(4), 1161–1166.

Cooper, D.N. et al., "Ectopic (Illegitimate) Transcription: New Possibilities for the Analysis and Diagnosis of Human Genetic Disease", *Ann. Med.*, 1994, 26(1), 9–14.

Field, M., "Role of Cyclic Nucleotides in Enterotoxic Diarrhea", *Adv. Cyclic Nucl. Res.*, 1980, 12, 267–277.

Giannella, R.A., "Pathogenesis of Acute Bacterial Diarrheal Disorders", *Ann. Rev. Med.*, 1981, 32, 341–357.

Kaplan, J.C. et al., "Illegitimate transcription: its use in the study of inherited disease", *Human Mutation*, 1992, 1(5), 357–360 (Abstract only).

Negrier, C. et al., "Illegitimate transcription: its use for studying genetic abnormalities in lymphoblastoid cells from patients with Glanzmann thrombasthenia", *British J. Haematology*, 1998, 100(1), 33–39.

Rao, M.C. et al., "Enterotoxins and Anti–toxins: Enterotoxins and ion transport", *Biochem. Sol. Trans.* 1984, 12, 177–180.

Zippelius, A. et al., "Limitations of Reverse–Transcriptase Polymerase Chain Reaction Analyses for Detection of Micrometastatic Epithelial Cancer Cells in Bone Marrow", *J. Clin. Oncology*, 1997, 15(7), 2701–2708.

METHODS OF AND KITS AND COMPOSITIONS FOR DIAGNOSING COLORECTAL TUMORS AND METASTASIS THEREOF

This Application is a continuation application of U.S. Ser. No. 09/046,178, filed Mar. 23, 1998, now U.S. Pat. No. 5,928,873, which is a continuation application of U.S. Ser. No. 08/789,270, filed Jan. 28, 1997, which issued Mar. 24, 1998 as U.S. Pat. No. 5,731,159, which is a continuation application of U.S. Ser. No. 08/305,056, filed Sep. 13, 1994, which issued Feb. 11, 1997 as U.S. Pat. No. 5,601,990.

FIELD OF THE INVENTION

The present invention relates to compositions and kits for and methods of detecting metastasized colorectal tumor cells in samples. The present invention also relates to compositions and kits for and methods of evaluating the extent of invasive activity of colorectal tumor cells in samples from the colon.

BACKGROUND OF THE INVENTION

Colorectal cancer is the third most common neoplasm worldwide and the second most common in the United States, representing about 15% of the newly diagnosed cases of cancer in the United States. The large intestine or large bowel is the third leading site for the development of new cancer and is diagnosed in about 150,000 patients each year. Colorectal cancer is the second leading cause of cancer-related deaths and is responsible for about 12% of cancer deaths in the United States. The mortality rate of newly diagnosed large bowel cancer approaches 50% and there has been little improvement over the past 40 years. Most of this mortality reflects local, regional and distant metastases. About thirty percent of patients with colorectal cancer have unresectable disease at presentation and about 40% develop metastases during the course of their disease. Distant metastatic disease is seen in liver (about 12%), lung (about 3%), bone (about 0.9%), brain (about 0.7%), nodes (about 4%), and peritoneum (about 2%) at the time of initial diagnosis. In 1987, the large bowel cancers found regionally or at distant sites at the time of diagnosis were about 26% and about 18%, respectively.

Surgery is the mainstay of treatment for colorectal cancer but recurrence is frequent. Colorectal cancer has proven resistant to chemotherapy, although limited success has been achieved using a combination of 5-fluorouracil and levamisole. Surgery has had the largest impact on survival and, in some patients with limited disease, achieves a cure. However, surgery removes bulk tumor, leaving behind microscopic residual disease which ultimately results in recrudescence. Overall recurrence rates for colonic tumors are about 33% and for rectal cancer about 42%. Of these recurrences, about 9% are local, about 13% are systemic metastatic disease, and the remaining 88% are a combination of local and systemic disease. Fifty percent of patients with recurrent colorectal cancer have hepatic metastases.

Early detection of primary, metastatic, and recurrent disease can significantly impact the prognosis of individuals suffering from colorectal cancer. Large bowel cancer diagnosed at an early stage has a significantly better outcome than that diagnosed at more advanced stages. The 5 year relative survival rates for patients with regional or distant metastases are 48% and 5%, compared with 90% and 77% for disease which is in situ or local, respectively, at the time of diagnosis. Similarly, diagnosis of metastatic or recurrent disease earlier potentially carries with it a better prognosis.

Immunoscintigraphy using monoclonal antibodies directed at tumor-specific markers has been employed to diagnose colorectal cancer. Monoclonal antibodies against carcinoembryonic antigen (CEA) labeled with $^{99}$Technetium identified 94% of patients with recurrent tumors. Similarly, $^{111}$Indium-labeled anti-CEA monoclonal antibodies successfully diagnosed 85% of patients with recurrent colorectal carcinoma who were not diagnosed by conventional techniques. $^{125}$Iodine-labeled antibodies have been effective in localizing more than 80% of the pathologically-confirmed recurrences by intraoperative gamma probe scanning.

There remains a need for compositions and kits which can specifically detect metastasized colorectal cancer cells using samples removed from or discharged by an individual being screened for, suspected of suffering from of suspected of being susceptible to metastasized colorectal tumors. There remains a need for methods of identifying individuals suffering from metastasized colorectal tumors using samples removed from or discharged by an individual being screened for, suspected of suffering from or suspected of being susceptible to metastasized colorectal tumors.

SUMMARY OF THE INVENTION

The present invention relates to in vitro methods of determining whether or not an individual has metastasized colorectal cancer cells. The present invention relates to in vitro methods of examining samples of non-colorectal tissue and body fluids from an individual to determine whether or not ST receptor protein, which is a protein that is specific to colorectal cells including colorectal tumor cells, is being expressed by cells outside of the colorectal track. The presence of the ST receptor protein or of nucleic acid molecules that are indicative of expression of the ST receptor protein is evidence that the individual is suffering from metastasized colorectal cancer.

The present invention relates to in vitro methods of determining whether or not tumor cells are colorectal in origin. The present invention relates to in vitro methods of diagnosing whether or not an individual suffering from cancer is suffering from colorectal cancer. The present invention relates to in vitro methods of examining samples of tumors from an individual to determine whether or not ST receptor protein, which is a protein that is specific to colorectal cells including colorectal tumor cells, is being expressed by the tumor cells. The presence of the ST receptor protein or of nucleic acid molecules that are indicative of expression of the ST receptor protein is evidence that the individual is suffering from colorectal cancer.

The present invention relates to in vitro kits for practicing the methods of the invention and to reagents and compositions useful to practice the methods, for example as components in such in vitro kits of the invention.

In some embodiments of the invention, non-colorectal tissue and fluid samples may be screened to identify the presence or absence of the ST receptor protein. Techniques such as an ST receptor/ligand binding assays, ELISA assays and Western blots may be performed to determine whether the ST receptor is present in a sample.

In some embodiments of the invention, non-colorectal tissue and fluid samples may be screened to identify whether ST receptor protein is being expressed in cells outside of the colorectal track by detecting the presence or absence of MRNA that encodes the ST receptor protein. The presence of mRNA that encodes the ST receptor protein or CDNA generated therefrom can be determined using techniques such as PCR amplification, Northern Blots (mRNA), Southern Blots (cDNA), or oligonucleotide hybridization.

In some embodiments of the invention, cells of non-colorectal tissue samples may be examined to identify the presence or absence of the ST receptor protein. Techniques such as an ST receptor/ligand binding or immunohistochemistry blots may be performed on tissue sections to determine whether the ST receptor is present in a sample.

In some embodiments of the invention, cells of non-colorectal tissue samples may be examined to determine whether ST receptor protein is being expressed in cells outside of the colorectal track by detecting the presence or absence of MRNA that encodes the ST receptor protein. The presence of MRNA that encodes the ST receptor/protein or CDNA generated therefrom in cells from tissue sections can be determined using techniques such as in situ hybridization.

Another aspect of the invention relates to methods of analyzing tissue samples from the colon tissue to evaluate the extent of metastasis or invasion of colorectal tumor cells into the laminapropria. The laminapropria represents the barrier between the colorectal tract and the rest of the body; see *Bailey's Textbook of Histology,* 16th edition, Coperhaven et al. 1975 Williams and Wilkens, Baltimore, Md. at page 404 which is incorporated herein by reference. By identifying the presence of ST receptor or mRNA that encodes ST receptor protein in cells of the laminapropria, the extent of invasion/infiltration of colorectal tumor cells into non-colorectal tissue can be evaluated and confirmed.

The present invention relates to in vitro kits for evaluating tissues samples to determine the level of metastasis and to reagents and compositions useful to practice the same. In some embodiments of the invention, tissue samples which include sections of the laminapropria may be isolated from individuals undergoing or recovery from surgery to remove colorectal tumors. The tissue is analyzed to determine the extent of invasion into the basement membrane of the laminapropria by neoplastic colorectal cells. Identification of the presence or absence of the ST receptor protein confirms evaluation of the migration of tumor cells into the basement membrane indicating metastasis. Techniques such as an ST receptor/ligand binding and immunohistochemistry assays may be performed to determine whether the ST receptor is present in cells in the tissue sample which are indicative of metastatic migration. Alternatively, in some embodiments of the invention, tissue samples that include the laminapropria are analyzed to identify whether ST receptor protein is being expressed in cells in the tissue sample which indicate metastatic migration by detecting the presence or absence of MRNA that encodes the ST receptor protein. The presence of MRNA that encodes the ST receptor protein or cDNA generated therefrom can be determined using techniques such as in situ hybridization.

DESCRIPTION OF PREFERRED EMBODIMENTS OF THE INVENTION

As used herein, the terms "ST" and "native ST" are used interchangeably and are meant to refer to heat-stable toxin (ST) which is a peptide produced by *E. coli,* as well as other organisms. STs are naturally occurring peptides which 1) are naturally produced by organisms, 2) which bind to the ST receptor and 3) which activate the signal cascade that mediates ST-induced diarrhea.

As used herein, the term "ST receptor" is meant to refer to the receptors found on, colorectal cells, including local and metastasized colorectal cancer cells, which bind to ST. In normal individuals, ST receptors are found exclusively in cells of intestine, in particular in cells in the duodenum, small intestine (jejunum and ileum), the large intestine, colon (cecum, ascending colon, transverse colon, descending colon and sigmoid colon) and rectum. The nucleotide sequence that encodes human ST receptor protein has been cloned and the amino acid and nucleotide sequences are described in U.S. Pat. No. 5,237,051 and F. J. Sauvage et al. 1991 *J. Biol. Chem.* 266:17912–17918, each of which is incorporated herein by reference.

As used herein, the term "ST receptor ligand" is meant to refer to compounds which specifically bind to the ST receptor. ST is an ST receptor ligand. An ST receptor ligand may be a peptide or a non-peptide. ST receptor ligands are described in U.S. patent application Ser. No. 08/141,892, filed Oct. 26, 1993, which is incorporated herein by reference.

As used herein, the term "ST receptor binding peptide" is meant to refer to ST receptor ligands that are peptides.

As used herein, the term "ST peptides" is meant to refer to ST receptor binding peptides described in U.S. patent application Ser. No. 08/141,892, filed Oct. 26, 1993.

As used herein, the term "fragment" is meant to refer to peptide a) which has an amino acid sequence identical to a portion of an ST receptor binding peptide and b) which is capable of binding to the ST receptor.

As used herein, the term "derivatve" is meant to refer to a peptide a) which has an amin acid sequence substantially identical to at least a portion of an ST receptor binding peptide and b) which is capable of finding to the ST receptor.

As used herein, the term "substantially identical" is meant to refer to an amino acid sequence that is the same as the amino acid sequence of an ST peptide except some of the residues are deleted or substituted with conservative amino acids or additional amino acids are inserted.

As used herein, the term "colorectal cancer" is meant to include the well-accepted medical definition that defines colorectal cancer as a medical condition characterized by cancer of cells of the intestinal tract below the small intestine (i.e. the large intestine (colon), including the cecum, ascending colon, transverse colon, descending colon, and sigmoid colon, and rectum). Additionally, as used herein, the term "colorectal cancer" is meant to further include medical conditions which are characterized by cancer of cells of the duodenum and small intestine (jejunum and ileum). The definition of colorectal cancer used herein is more expansive than the common medical definition but is provided as such since the cells of the duodenum and small intestine also contain ST receptors and are therefore amenable to the methods of the present invention using the compounds of the present invention.

As used herein, the term "metastasis" is meant to refer to the process in which cancer cells originating in one organ or part of the body relocate to another part of the body and continue to replicate. Metastasized cells subsequently form tumors which may further metastasize. Metastasis thus refers to the spread of cancer from the part of the body where it originally occurs to other parts of the body. The present invention relates to methods of delivering active agents to metastasized colorectal cancer cells.

As used herein, the term "metastasized colorectal cancer cells" is meant to refer to colorectal cancer cells which have metastasized; colorectal cancer cells localized in a part of the body other than the duodenum, small intestine jejunum and ileum), large intestine (colon), including the cecum, ascending colon, transverse colon, descending colon, and sigmoid colon, and rectum.

As used herein, the term"non-colorectal sample" and "extra-intestinal sample" are used interchangeably and meant to refer to a sample of tissue or body fluid from a source other than colorectal tissue. In some preferred embodiments, the non-colorectal sample is a sample of tissue such as lymph nodes. In some preferred embodiments, the non-colorectal sample is a sample of extra-intestinal tissue which is an adenocarcinoma of unconfirmed origin. In some preferred embodiments, the non-colorectal sample is a blood sample.

As used herein, "an individual suffering from an adenocarcinoma of unconfirmed origin" is meant to refer to an individual who has a tumor in which the origin has not been definitively identified.

As used herein, "an individual is suspected of being susceptible to metastasized colorectal cancer" is meant to refer to an individual who is at a particular risk of developing metastasized colorectal cancer. Examples of individuals at a particular risk of developing metastasized colorectal cancer are those whose family medical history indicates above average incidence of colorectal cancer among family members and/or those who have already developed colorectal cancer and have been effectively treated who therefore face a risk of relapse and recurrence.

Advancements in the understanding of genetics and developments in technology as well as epidemiology allow for the determination of probability and risk assessment an individual has for developing colorectal cancer. Using family health histories and/or genetic/screening, it is possible to estimate the probability that a particular individual has for developing certain types of cancer including colorectal cancer. Those individuals that have been identified as being predisposed to developing a particular form of cancer can be monitored or screened to detect evidence of metastasized colorectal cancer. Upon discovery of such evidence, early treatment can be undertaken to combat the disease.

Similarly, those individuals who have already developed colorectal cancer and who have been treated to remove the cancer or are otherwise in remission are particularly susceptible to relapse and reoccurrence including the metastasis of tumors. Such individuals can be monitored and screened to detect evidence of metastasis and upon discovery of such evidence, early treatment can be undertaken to combat the disease.

ST, which is produced by *E. coli*, as well as other organisms, is responsible for endemic diarrhea in developing countries and travelers diarrhea. ST induces intestinal secretion by binding to specific receptors, ST receptors, in the apical brush border membranes of the mucosal cells lining the intestinal tract. Binding of ST to ST receptors is non-covalent and occurs in a concentration-dependent and saturable fashion. Once bound, ST-ST receptor complexes appear to be internalized by intestinal cells, i.e. transported from the surface into the interior of the cell. Binding of ST to ST receptors triggers a cascade of biochemical reactions in the apical membrane of these cells resulting in the production of a signal which induces intestinal cells to secrete fluids and electrolytes, resulting in diarrhea.

ST receptors are unique in that they are only localized in the apical brush border membranes of the cells lining the intestinal tract. Indeed, they are not found in any other cell type in placental mammals. In addition, ST receptors are almost exclusively localized to the apical membranes, with little being found in the basolateral membranes on the sides of intestinal cells.

Mucosal cells lining the intestine are joined together by tight junctions which form a barrier against the passage of intestinal contents into the blood stream and components of the blood stream into the intestinal lumen.

In individuals suffering from colorectal cancer, the cancer cells are often derived from cells that produce and display the ST receptor and these cancer cells continue to produce and display the ST receptor on their cell surfaces. Indeed, T84 cells, which are human colonic adenocarcinoma cells isolated from lung metastases, express ST receptors on their cell surface. Similarly, HT29glu-cells, which are human colonic adenocarcinoma cells, express receptors for ST. Thus, in individuals suffering from colorectal cancer, some metastasized intestinal cancer cells express ST receptors.

An effort was undertaken to determine the proportion of colorectal tumors which have the ST receptor. Each of the tumors tested were independently confirmed to be colorectal cancer by standard techniques of surgical pathology. Every one of the colorectal cancer tumors tested, including local colorectal tumors and metastasized tumors (liver, lung, lymphnode, peritoneum, gall bladder), possessed ST receptors. In each case, the affinity and density of receptors was amenable for targeting. That is, the cells possessed at least $10^4$–$10^6$ receptors per cell and demonstrated an affinity of $10^{-7}$ or better (that is preferably between $10^{-8}$ to $10^{-9}$ or less; the lower number indicating a tighter bond, thus a higher affinity). Normal liver, lymphnode, peritoneum and lung cells were found not to possess ST receptors.

When such cancer cells metastasize, the metastasized cancer cells continue to produce and display the ST receptor. The expression of ST receptors on the surfaces of metastatic tumors provides a target for selective binding of conjugated compositions. ST receptors permit the absolutely specific targeting of diagnostic agents to metastatic colorectal cancer cells.

In some embodiments, diagnostic methods and kits of the present invention are specifically targeted to detecting metastatic disease. In other embodiments, methods and kits are provided for evaluating whether or not a tumor is colorectal in origin. In other embodiments, methods and kits are provided for evaluating the metastatic migration of tumor cells in the laminapropria; indicating the level of invasion of colorectal tumor cells into the basement membrane.

According to the invention, compounds are provided which bind to ST receptor protein or mRNA encoding the receptor. Normal tissue in the body does not have ST receptors or mRNA encoding ST receptors except cells of the intestinal tract. Thus, if non-colorectal samples possess ST receptors metastasis of colorectal tumor cells is indicated. Thus, metastasized colorectal cells may be identified by detecting in non-colorectal samples ST receptors or mRNA encoding ST receptors. The expression of ST receptor is a marker for cell type and allows for the identification of colorectal metastasis in extra-intestinal samples. Moreover, expression of ST receptor is a marker for cell type and allows for the identification of the origin of adenocarcinoma of unconfirmed origin as colorectal tumors. Additionally, expression of ST receptor is useful to visualize and confirm the invasion of colorectal neoplasms into the basement membrane of the laminapropria.

Patients
Patients with Adenocarcinomas

The invention can be used to identify colorectal tumors in samples of tumors removed from individuals suffering from adenocarcinomas of unconfirmed origin.

Screening/Monitoring Patients

Individuals who are at risk for developing metastasized colorectal cancer may be screened using the in vitro diagnostic methods of the present invention. The invention is particularly useful for monitoring individuals whose family medical history includes relatives who have suffered from colorectal cancer. Likewise, the invention is useful to monitor individuals who/have been diagnosed as having colorectal cancer and, particularly those who have been treated and had tumors removed and/or are otherwise experiencing remission.

Surgical Patients to be Evaluated

For aspects of the invention related to analysis of lumen tissue, the invention is useful to evaluate the level of metastatic migration of colorectal tumor cells using lumen samples taken from surgery patients at and near the site of the tumor.

Samples

Tissue Samples

Non-colorectal tissue samples may be obtained from any tissue except those of the colorectal track, i.e. the intestinal tract below the small intestine (i.e. the large intestine (colon), including the cecum, ascending colon, transverse colon, descending colon, and sigmoid colon, and rectum) and additionally the duodenum and small intestine (jejunum and ileum). The cells of all tissue except those of the colorectal track do not express the ST receptor. Thus if the ST receptor protein or mRNA encoding the ST receptor protein are detected in non-colorectal samples, the presence of metastatic colorectal cancer cells is indicated. In some preferred embodiments, the tissue samples are lymph nodes.

Tissue samples may be obtained by standard surgical techniques including use of biopsy needles. One skilled in the art would readily appreciate the variety of test samples that may be examined for ST receptor protein and recognize methods of obtaining tissue samples.

Tissue samples may be homogenized or otherwise prepared for screening for the presence of ST receptor protein by well known techniques such as sonication, mechanical disruption, chemical lysis such as detergent lysis or combinations thereof.

Tumor Samples

Samples from tumors may be identified as colorectal in origin by identification of expression of ST receptors using the methods of the invention. Simples of tumors removed from individuals suffering from adenocarcinomas of unconfirmed origin can be tested to determine whether or not they possess ST receptor protein or mMA encoding ST receptor protein. If the sample is removed from the intestinal track, a section of frozen cells can be examined to determine if the tumor cells express ST receptor protein. If the sample is removed from be extra-intestinal tissue, a section of frozen cells can be examined to determine if the tumor cells express ST receptor protein or the sample can be homogenized and tested since the non-cancer cells will not possess ST receptor and therefore not present background.

Samples may be obtained from resected tissue or biopsy material including needle biopsy. Tissue section preparation for surgical pathology may be frozen and prepared using standard techniques. In ST binding assays on tissue sections, ST is added before fixing cells. Immunohistochemistry and in situ hybridization binding assays on tissue sections are performed in fixed cells. Extra-intestinal samples may be homogenized by standard techniques such as sonication, mechanical disruption or chemical lysis such as detergent lysis. It is also contemplated that tumor samples in body such as blood, urine, lymph fluid, cerebral spinal fluid, amniotic fluid, vaginal fluid, semen and stool samples may also be screened to determine if such tumors are colorectal in origin.

Body Fluid Samples

Examples of body fluid samples include blood, urine, lymph fluid, cerebral spinal fluid, amniotic fluid, vaginal fluid and semen. In some preferred embodiments, blood is used as a sample of body fluid. Cells may be isolated from fluid sample such as centrifugation. One skilled in the art would readily appreciate the variety of test samples that may be examined for ST receptor protein. Test samples may be obtained by such methods as withdrawing fluid with a syringe or by a swab. One skilled in the art would readily recognize other methods of obtaining test samples.

In an assay using a blood sample, the blood plasma may be separated from the blood cells. The blood plasma may be screened for St receptor protein including truncated protein which is released into the blood when the ST receptor protein is cleaved from or sloughed off from metastasized colorectal tumor cells. In some embodiments, blood cell fractions are screened for the presence of metastasized colorectal tumor cells. In some embodiments, lymphocytes present in the blood cell fraction are screened by lysing the cells and detecting the presence of ST receptor protein or mRNA encoding ST receptor protein which may be present as a result of the presence of any metastasized colorectal tumor cells that may have been engulfed by the blood cell.

Laminapropria Tissue Samples

Samples of the laminapropria are removed during colorectal tumor removal surgery such as by resection or colonoscopy. The sample including basement membrane cells is frozen. If an ST binding assay is to be performed, the labelled ST is contacted to the frozen section and the cells are then fixed and stained. If immunohistochemistry or in situ hybridization is to be performed, the frozen section is stained and then the assay is run. Those having ordinary skill in the art can readily isolate samples which include portions of the laminapropria and fix and stain them using standard techniques. By adding the visualization provided with an ST receptor detection technique, the section can be more comprehensively analyzed and the level of invasion of neoplastic colorectal cells into the laminapropria can be determined. The present invention may be used to analyze and evaluate the extent of progression of localized colorectal tumors, that is primary or non-metastatic colorectal tumors if these have penetrated the basement membrane underlying the mucosa into the submucosa.

Assays

Immunoassay

The present invention relates to immunoassay methods of identifying individuals suffering from colorectal cancer metastasis by detecting presence of ST receptor protein in sample of non-colorectal tissue or body fluid using antibodies which were produced in response to exposure to ST receptor protein.

The present invention also relates to immunoassay methods of identifying individuals suffering from colorectal cancer by detecting presence of ST receptor protein in sample of tumor using antibodies which were produced in response to exposure to ST receptor protein.

The antibodies are preferably monoclonal antibodies. The antibodies are preferably raised against ST receptor protein made in human cells. Immunoassays are well known and there design may be routinely undertaken by those having ordinary skill in the art. Those having ordinary skill in the art can produce monoclonal antibodies which specifically bind to ST receptor protein and are useful in methods and kits of the invention using standard techniques and readily available starting materials. The techniques for producing monoclonal antibodies are outlined in Harlow, E. and D. Lane, (1988) *ANTIBODIES: A Laboratory Manual,* Cold Spring Harbor Laboratory, Cold Spring Harbor N.Y., which is incorporated herein by reference, provide detailed guidance for the production of hybridomas and monoclonal antibodies which specifically bind to target proteins. It is within the scope of the present invention to include FAbs and F(Ab)2s which specifically bind to ST receptor in place of antibodies.

Briefly, the ST receptor protein is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to the ST receptor protein, the hybridoma which produces them is cultured to produce a continuous supply of anti-St receptor protein specific antibodies.

The present invention relates to antibodies which are produced in response to exposure to ST receptor protein. The antibodies are preferably monoclonal antibodies. The antibodies are preferably raised against ST receptor protein made in human cells. In some embodiments, antibodies specifically bind to the extracellular domain of ST receptor protein. In some embodiments, antibodies specifically bind to the transmembrane domain. In some embodiments, antibodies specifically bind to the cytoplasmic domain.

The means co detect the presence of a protein in a test sample are routine and one having ordinary skill in the art can detect the presence or absence of a protein or an antibody using well known methods. One well known method of detecting the presence of a protein is an immunoassay. One having ordinary skill in the art can readily appreciate the multitude of ways to practice an immunoassay to detect the presence of ST receptor protein in a sample.

According to some embodiments, immunoassays comprise allowing proteins in the sample to bind a solid phase support such as a plastic surface. Detectable antibodies are then added which selectively binding to either the ST receptor protein. Detection of the detectable antibody indicates the presence of ST receptor protein. The detectable antibody may be a labeled or an unlabelled antibody. Unlabelled antibody may be detected using a second, labelled antibody that specifically binds to the first antibody or a second, unlabelled antibody which can be detected using labelled protein A, a protein that complexes with antibodies. Various immunoassay procedures are described in *Immunoassays for the 80's*, A. Voller et al., Eds.., University Park, 1981, which is incorporated herein by reference.

Simple immunoassays may be performed in which a solid phase support is contacted with the test sample. Any proteins present in the test sample bind the solid phase support and can be detected by a specific, detectable antibody preparation. Such a technique is the essence of the dot blot, Western blot and other such similar assays.

Other immunoassays may be more complicated but actually provide excellent results. Typical and preferred immunometric assays include "forward" assays for the detection of a protein in which a first anti-protein antibody bound to a solid phase support is contacted with the test sample. After a suitable incubation period, the solid phase support is washed to remove unbound protein. A second, distinct anti-protein antibody is then added which is specific for a portion of the specific protein not recognized by the first antibody. The second antibody is preferably detectable. After a second incubation period to permit the detectable antibody to complex with the specific protein bound to the solid phase support through the first antibody, the solid phase support is washed a second time to remove the unbound detectable antibody. Alternatively, the second antibody may not be detectable. In this case, a third detectable antibody, which binds the second antibody is added to the system. This type of "forward sandwich" assay may be a simple yes/no assay to determine whether binding has occurred or may be made quantitative by comparing the amount of detectable antibody with that obtained in a control. Such "two-site" or "sandwich" assays are described by Wide, *Radioimmune Assay Method,* Kirkham, Ed., E. & S. Livingstone, Edinburgh, 1970, pp. 199–206, which is incorporated herein by reference.

Other types of immunometric assays are the so-called "simultaneous" and "reverse" assays. A simultaneous assay involves a single incubation step wherein the first antibody bound to the solid phase support, the second, detectable antibody and the test sample are added at the same time. After the incubation is completed, the solid phase support is washed to remove unbound proteins. The presence of detectable antibody associated with the solid support is then determined as it would be in a conventional "forward sandwich" assay. The simultaneous assay may also be adapted in a similar manner for the detection of antibodies in a test sample.

The "reverse" assay comprises the stepwise addition of a solution of detectable antibody to the test sample followed by an incubation period and the addition of antibody bound to a solid phase support after an additional incubation period. The solid phase support is washed in conventional fashion to remove unbound protein/antibody complexes and unreacted detectable antibody. The determination of detectable antibody associated with the solid phase support is then determined as in the "simultaneous" and "forward" assays. The reverse assay may also be adapted in a similar manner for the detection of antibodies in a test sample.

The first component of the immunometric assay may be added to nitrocellulose or other solid phase support which is capable of immobilizing proteins. The first component for determining the presence of ST receptor in a test sample is anti-ST receptor antibody. By "solid phase support" or "support" is intended any material capable of binding proteins. Well-known solid phase supports include glass, polystyrene, polypropylene, polyethylene, dextran, nylon, amylases, natural and modified celluloses, polyacrylamides, agaroses, and magnetite. The nature of the support can be either soluble to some extent or insoluble for the purposes of the present invention. The support configuration may be spherical, as in a bead, or cylindrical, as in the inside surface of a test tube or the external surface of a rod. Alternatively, the surface may be flat such as a sheet, test strip, etc. Those skilled in the art will know many other suitable "solid phase supports" for binding proteins or will be able to ascertain the same by use of routine experimentation. A preferred solid phase support is a 96-well microtiter plate.

To detect the presence of ST receptor protein, detectable anti-ST receptor antibodies are used. Several methods are well known for the detection of antibodies.

One method in which the antibodies can be detectably labeled is by linking the antibodies to an enzyme and subsequently using the antibodies in an enzyme immunoassay (EIA) or enzyme-linked immunosorbent assay (ELISA), such as a capture ELISA. The enzyme, when subsequently exposed to its substrate, reacts with the substrate and generates a chemical moiety which can be detected, for example, by spectrophotometric, fluorometric or visual means. Enzymes which can be used to detectably label antibodies include, but are not limited to malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. One skilled in the art would readily recognize other enzymes which may also be used.

Another method in which antibodies can be detectably labeled is through radioactive isotopes and subsequent use in a radioimmunoassay (RIA) (see, for example, Work, T. S. et al., *Laboratory Techniques and Biochemistry in Molecular Biology,* North Holland Publishing Company, N.Y., 1978, which is incorporated herein by reference). The radioactive isotope can be detected by such means as the use of a gamma counter or a scintillation counter or by autoradiography. Isotopes which are particularly useful for the purpose of the present invention are $^3H$, $^{125}I$, $^{131}I$, $^{35}S$, and $^{14}C$. Preferably $^{125}I$ is the isotope. One skilled in the art would readily recognize other radioisotopes which may also be used.

It is also possible to label the antibody with a fluorescent compound. When the fluorescent-labeled antibody is exposed to light of the proper wave length, its presence can be detected due to its fluorescence. Among the most commonly used fluorescent labeling compounds are fluorescein isothiocyanate, rhodamine, phycoerythrin, phycocyanin, allophycocyanin, ophthaldehyde and fluorescamine. One skilled in the art would readily recognize other fluorescent compounds which may also be used.

Antibodies can also be detectably labeled using fluorescence-emitting metals such as $^{152}Eu$, or others of the lanthanide series. These metals can be attached to the protein-specific antibody using such metal chelating groups as diethylenetriaminepentaacetic acid (DTPA) or ethylenediaminetetraacetic acid (EDTA). One skilled in the art would readily recognize other fluorescence-emitting metals as well as other metal chelating groups which may also be used.

Antibody can also be delectably labeled by coupling to a chemiluminescent compound. The presence of the chemiluminescent-labeled antibody is determined by detecting the presence of luminescence that arises during the course of a chemical reaction. Examples of particularly useful chemoluminescent labeling compounds are luminol, isoluminol, theromatic acridinium ester, imidazole, acridinium salt and oxalate ester. One skilled in the art would readily recognize other chemiluminescent compounds which may also be used.

Likewise, a bioluminescent compound may be used to label antibodies. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin. One skilled in the art would readily recognize other bioluminescent compounds which may also be used.

Detection of the protein-specific antibody, fragment or derivative may be accomplished by a scintillation counter if, for example, the detectable label is a radioactive gamma emitter. Alternatively, detection may be accomplished by a fluorometer if, for example, the label is a fluorescent material. In the case of an enzyme label, the detection can be accomplished by colorometric methods which employ a substrate for the enzyme. Detection may also be accomplished by visual comparison of the extent of enzymatic reaction of a substrate in comparison with similarly prepared standards. One skilled in the art would readily recognize other appropriate methods of detection which may also be used.

The binding activity of a given lot of antibodies may be determined according to well known methods. Those skilled in the art will be able to determine operative and optimal assay conditions for each determination by employing routine experimentation.

Positive and negative controls may be performed in which known amounts of ST receptor protein and no ST receptor protein, respectively, are added to assays being performed in parallel with the test assay. One skilled in the art would have the necessary knowledge to perform the appropriate controls.

ST receptor protein may be produced as a reagent for positive controls routinely. One skilled in the art would appreciate the different manners in which the ST receptor protein may be produced and isolated.

An "antibody composition" refers to the antibody or antibodies required for the detection of the protein. For example, the antibody composition used for the detection of ST receptor in a test sample comprises a first antibody that binds ST receptor protein as well as a second or third detectable antibody that binds the first or second antibody, respectively.

To examine a test sample for the presence of ST receptor protein, a standard immunometric assay such as the one described below may be performed. A first anti-ST receptor protein antibody, which recognizes a specific portion of ST receptor such as the extracellular or cytoplasmic portion, is added to a 96-well microtiter plate in a volume of buffer. The plate is incubated for a period of time sufficient for binding to occur and subsequently washed with PBS to remove unbound antibody. The plate is then blocked with a PBS/BSA solution to prevent sample proteins from nonspecifically binding the microtiter plate. Test sample are subsequently added to the wells and the plate is incubated for a period of time sufficient for binding to occur. The wells are washed with PBS to remove unbound protein. Labeled anti-ST receptor antibodies, which recognize portions of ST receptor not recognized by the first antibody, are added to the wells. The plate is incubated for a period of time sufficient for binding to occur and subsequently washed with PBS to remove unbound, labeled anti-ST receptor antibody. The amount of labeled and bound anti-St receptor antibody is subsequently determined by standard techniques.

Kits which are useful for the detection of ST receptor in a test sample comprise a container comprising anti-ST receptor antibodies and a container or containers comprising controls. Controls include one control sample which does not contain ST receptor protein and/or another control sample which contained ST receptor protein. The anti-ST receptor antibodies used in the kit are detectable such as being detectably labelled. If the detectable anti-ST antibody is not labelled, it may be detected by second antibodies or protein A for example which may also be provided in some kits in separate containers. Additional components in some kits include solid support, buffer, and instructions for carrying out the assay.

The immunoassay is useful for detecting ST receptor in homogenized tissue samples and body fluid samples including the plasma portion or cells in the fluid sample.

Western Blots

The present invention relates to methods of identifying individuals suffering from colorectal cancer metastasis by detecting presence of ST receptor protein in sample of non-colorectal tissue or body fluid using Western blots. Western blots use detectable anti-ST receptor antibodies to bind to any ST receptor present in a sample and thus indicate the presence of the receptor in the sample.

The present invention also relates to methods of identifying individuals suffering from colorectal cancer using Western blots to detect presence of ST receptor protein in sample of tumor using antibodies which were produced in response to exposure to ST receptor protein.

Western blot techniques, which are described in Sambrook, J. et al., (1989) *Molecular Cloning: A Laboratory Manual,* Cold Spring Harbor Laboratory Press, Cold Spring Harbor, N.Y., which is incorporated herein by reference, are similar to immunoassays with the essential difference being that prior to exposing the sample to the antibodies, the proteins in the samples are separated by gel electrophoresis and the separated proteins are then probed with antibodies. In some preferred embodiments, the matrix is an SDS-PAGE gel matrix and the separated proteins in the matrix are transferred to a carrier such as filter paper prior to probing with antibodies. Anti-ST receptor antibodies described above are useful in Western blot methods.

Generally, samples are homogenized and cells are lysed using detergent such as Triton-X. The material is then separated by the standard techniques in Sambrook, J. et al., (1989) *Molecular Cloning: A Laboratory Manual,* Cold Spring Harbor Laboratory Press, Cold Spring Harbor, N.Y.

Kits which are useful for the detection of ST receptor in a test sample by western Slot comprise a container comprising anti-ST receptor antibodies and a container or containers comprising controls. Controls include one control sample which does not contain ST receptor protein and/or another control sample which contained ST receptor protein. The anti-ST receptor antibodies used in the kit are detectable such as being detectably labelled. If the detectable anti-ST antibody is not labelled, it may be detected by second antibodies or protein A for example which may also be provided in some kits in separate containers. Additional components in some kits include instructions for carrying out the assay.

Western blots are useful for detecting ST receptor in homogenized tissue samples and body fluid samples including the plasma portion or cells in the fluid sample.

ST Binding Assay

The present invention relates to methods of identifying individuals suffering from colorectal cancer metastasis by detecting presence of ST receptor protein in sample of non-colorectal tissue or body fluid using an ST receptor binding assay. The ST receptor binding assay uses a detectable ST receptor ligand to bind to any ST receptor present and thus indicate the presence of the receptor in a sample.

The present invention also relates to methods of identifying individuals suffering from colorectal cancer by detecting presence of ST receptor protein in sample of tumor.

In some embodiments, the ST receptor ligand may be native ST. Native ST isolated from *E. coli* is 18 or 19 amino acids in length. The smallest "fragment" of ST which retains activity is the 13 amino acid core peptide extending toward the carboxy terminal from cysteine 6 to cysteine 18 (of the 19 amino acid form). Analogues of ST have been generated by cloning and by chemical techniques. Small peptide fragments of the native ST structure which include the structural determinant that confers binding activity may be constructed. Once a structure is identified which binds to ST receptors, non-peptide analogues mimicking that structure in space are designed. U.S. patent application Ser. No. 08/141,892, filed Oct. 26, 1993, which is incorporated herein by reference, describes the amino acid sequences of such compounds including derivatives thereof having substantially identical amino acid sequences of ST peptides with deletions and/or insertions and/or conservative substitutions of amino acids and/or comprising D amino acids.

The ST receptor binding assay can be readily performed by those having ordinary skill in the art using readily available starting materials. ST receptor binding assays may be performed a variety of ways but each essentially identify whether or not an ST receptor protein is present in a sample by determining whether or not a detectable ST receptor ligand binds to a receptor in a sample. Briefly, the assay consists of incubating a sample with a constant concentration of an ST ligand such as $1 \times 10^{-10}$ M to $5 \times 10^{-10}$ M of $^{125}$I-ST. As a control, a duplicate preparation of a sample known to contain ST receptors are incubated with a duplicate concentration of $^{125}$I-ST. Assays are incubated to equilibrium (for example 2 hours) and the sample is analyzed to determine whether or not $^{125}$I-ST is bound to material in the sample. The $^{125}$I-ST/sample is passed through a filter which is capable of allowing $^{125}$I-ST to pass through but not capable of allowing ST receptor to pass through. Thus, if ST receptor is present in the sample, it will bind the $^{125}$I-ST which will then be trapped by the filter. Detection of $^{125}$I-ST in the filter indicates the presence of ST receptor in the sample. In some preferred embodiments, the filter is Whitman GFB glass filter paper. Controls include using samples which are known to contain ST receptors, e.g. intestinal membranes from rat intestine, human intestine, T84 cells, isolated ST receptor protein or cells expressing cloned nucleotide sequence encoding ST receptor proteins.

ST may be isolated from natural sources using standard techniques. Additionally, ST receptor binding peptides and conjugated compositions or portions thereof which are peptides may be prepared routinely by any of the following known techniques.

In addition to being conjugated to $^{125}$I, ST may be detectable by binding it to other radionuclides such as $^{43}$K, $^{52}$Fe, $^{57}$Co, $^{67}$Cu, $^{67}$Ga, $^{68}$Ga, $^{77}$Br, $^{81}$Rb/$^{81M}$Kr, $^{87M}$Sr, $^{99M}$Tc, $^{111}$In, $^{113M}$In, $^{123}$I, $^{125}$I, $^{127}$Cs, $^{129}$Cs, $^{131}$I, $^{132}$I, $^{197}$Hg, $^{203}$Pb and $^{206}$Bi, $^{47}$Sc, $^{67}$Cu, $^{90}$Y, $^{109}$Pd, $^{123}$I, $^{125}$I, $^{131}$I, $^{186}$Re, $^{188}$Re, $^{199}$Au, $^{211}$At, $^{212}$Pb, $^{212}$B, $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193M}$Pt and $^{197}$Hg or by binding it to other labels such as fluorescein or enzymes. Each of the labelling means described above for detectably labelling antibodies can be adapted to label ST receptor ligands and are considered to be described as such herein.

Kits include containers comprising detectable ST receptor ligand together with containers having positive and/or negative controls, i.e. samples which contain ST receptor and samples which contain no ST receptor, respectively. The detectable ST receptor ligand is preferably labelled. Additional components in some kits include solid support, buffer, and instructions for carrying out the assay.

The ST receptor binding assay is useful for detecting ST receptor in homogenized tissue samples and body fluid samples including the plasma portion or cells in the fluid sample.

Nucleotide Sequence Based Detection

Aspects of the present invention include various methods of determining whether a sample contains cells that express ST receptor by sequence-based molecular analysis. Several different methods are available for doing so including those using Polymerase Chain Reaction (PCR) technology, using Northern blot technology, oligonucleotide hybridization technology, and in situ hybridization technology.

The invention relates to oligonucleotide probes and primers used in the methods of identifying mRNA that encodes ST receptor and to diagnostic kits which comprise such components.

The mRNA sequence-based methods for determining whether a sample mRNA encoding ST receptor include but are not limited to polymerase chain reaction technology, Northern and Southern blot technology, in situ hybridization technology and oligonuclectide hybridization technology.

The methods described herein are meant to exemplify how the present invention may be practiced and are not meant to limit the scope of invention. It is contemplated that other sequence-based methodology for detecting the presence of specific mRNA that encodes ST receptor in non-colorectal samples may be employed according to the invention.

A preferred method to detecting mRNA that encodes ST receptor in genetic material derived from non-colorectal samples uses polymerase chain reaction (PCR) technology. PCR technology is practiced routinely by those having ordinary skill in the art and its uses in diagnostics are well known and accepted. Methods for practicing PCR technology are disclosed in "PCR Protocols: A Guide to Methods and Applications", Innis, M. A., et al. Eds. Academic Press, Inc. San Diego, Calif. (1990) which is incorporated herein by reference. Applications of PCR technology are disclosed in "Polymerase Chain Reaction" Erlich, H. A., et al., Eds. Cold Spring Harbor Press, Cold Spring Harbor, N.Y. (1989) which is incorporated herein by reference. U.S. Pat. Nos. 4,683,202, 4,683,195, 4,965,188 and 5,075,216, which are each incorporated herein by reference describe methods of performing PCR. PCR may be routinely practiced using Perkin Elmer Cetus GENE AMP RNA PCR kit, Part No. N808-0017.

PCR technology allows for the rapid generation of multiple copies of DNA sequences by providing 5' and 3' primers that hybridize to sequences present in an RNA or DNA molecule, and further providing free nucleotides and an enzyme which fills in the complementary bases to the nucleotide sequence between the primers with the free nucleotides to produce a complementary strand of DNA. The enzyme will fill in the complementary sequences adjacent to the primers. If both the 5' primer and 3' primer hybridize to nucleotide sequences on the same small fragment of nucleic acid, exponential amplification of a specific double-stranded size product results. If only a single primer hybridizes to the nucleic acid fragment, linear amplification produces single-stranded products of variable length.

The nucleoctide sequence encoding ST receptor protein is well known such as in U.S. Pat. No. 5,237,051 and F. J. Sauvage et al. 1991 *J. Biol. Chem.* 266:17912–17918. To perform this method, RNA is extracted from cells in a sample and tested or used to make cDNA using well known methods and readily available starting materials.

The mRNA or cDNA is combined with the primers, free nucleotides and enzyme following standard PCR protocols. The mixture undergoes a series of temperature changes. If the mRNA or cDNA encoding ST receptor is present, that is, if both primers hybridize to sequences on the same molecule, the molecule comprising the primers and the intervening complementary sequences will be exponentially amplified. The amplified DNA can be easily detected by a variety of well known means. If the chimeric gene is not present, no DNA molecule will be exponentially amplified. Rather, amplification of wild-type transcript will yield low levels of variable length product. The PCR technology therefore provides an extremely easy, straightforward and reliable method of detecting mRNA encoding ST receptor protein in a sample.

PCR primers can be designed routinely by those having ordinary skill in the art using well known cDNA sequence information. Primers are generally 8–50 nucleotides, preferably 18–28 nucleotides. A set of primers contains two primers. When performing PCR on extracted mRNA or cDNA generated therefrom, if the mRNA, or cDNA encoding ST receptor protein is present, multiple copies of the mRNA or cDNA will be made. If it is not present, PCR will not generate a discrete detectable product.

PCR product, i.e. amplified DNA, may be detected by several well known means. The preferred method for detecting the presence of amplified DNA is to separate the PCR reaction material by gel electrophoresis and stain the gel with ethidium bromide in order to visual the amplified DNA if present. A size standard of the expected size of the amplified DNA is preferably run on the gel as a control.

In some instances, such as when unusually small amounts of RNA are recovered and only small amounts of cDNA are generated therefrom, it is desirable or necessary to perform a PCR reaction on the first PCR reaction product. That is, if difficult to detect quantities of amplified DNA are produced by the first reaction, a second PCR can be performed to make multiple copies of DNA sequences of the first amplified DNA. A nested set of primers are used in the second PCR reaction. The nested set of primers hybridize to sequences downstream of the 5' primer and upstream of the 3' primer used in the first reaction.

The present invention includes oligonucleotide which are useful as primers for performing PCR methods to amplify mRNA or cDNA that encodes ST receptor protein.

According to the invention, diagnostic kits can be assembled which are useful to practice methods of detecting the presence of mRNA or cDNA that encodes ST receptor in non-colorectal samples. Such diagnostic kits comprise oligonucleotide which are useful as primers for performing PCR methods. It is preferred that diagnostic kits according to the present invention comprise a container comprising a size marker to be run as a standard on a gel used to detect the presence of amplified DNA. The size marker is the same size as the DNA generated by the primers in the presence of the mRNA or cDNA encoding ST receptor.

PCR assays are useful for detecting mRNA encoding ST receptor in homogenized tissue samples and cells in body fluid samples. It is contemplated that PCR on the plasma portion of a fluid sample could be used to detect mRNA encoding ST receptor protein.

Another method of determining whether a sample contains cells expressing ST receptor is by Northern Blot analysis of mRNA extracted from a non-colorectal sample. The techniques for performing Northern blot analyses are well known by those having ordinary skill in the art and are described in Sambrook, J. et al., (1989) *Molecular Cloning: A Laboratory Manual,* Cold Scring Harbor Laboratory Press, Cold Spring Harbor, N.Y. mRNA extraction, electrophoretic separation of the mRNA, blotting, probe preparation and hybridization are all well known techniques that can be routinely performed using readily available starting material.

One having ordinary skill in the art, performing routine techniques, could design probes to identify mRNA encoding ST receptor using the information in U.S. Pat. No. 5,237,051 and F. J. Sauvage et al. 1991 *J. Biol. Chem.* 266:17912–17918.

The mRNA is extracted using poly dT columns and the material is separated by electrophoresis and, for example, transferred to nitrocellulose paper. Labelled probes made from an isolated specific fragment or fragments can be used to visualize the presence of a complementary fragment fixed to the paper.

According to the invention, diagnostic kits can be assembled which are useful to practice methods of detecting the presence of mRNA that encodes ST receptor in non-colorectal samples by Northern blot analysis. Such diagnostic kits comprise oligonucleotide which are useful as probes for hybridizing to the mRNA. The probes may be radiolabelled. It is preferred that diagnostic kits according to the present invention comprise a container comprising a size marker to be run as a standard on a gel. It is preferred that diagnostic kits according to the present invention comprise a container comprising a positive control which will hybridize to the probe.

Northern blot analysis is useful for detecting mRNA encoding ST receptor in homogenized tissue samples and cells in body fluid samples. It is contemplated that PCR on the plasma portion of a fluid sample could be used to detect mRNA encasing ST receptor protein.

Another method of detecting the presence of mRNA encoding ST receptor protein by oligonucleotide hybridization technology. Oligonucleotide hybridization technology is well known to those having ordinary skill in the art. Briefly, detectable probes which contain a specific nucleotide sequence that will hybridize to nucleotide sequence of mRNA encoding ST receptor protein. RNA or cDNA made from RNA from a sample is fixed, usually to filter paper or the like. The probes are added and maintained under conditions that permit hybridization only if the probes fully complement the fixed genetic material. The conditions are sufficiently stringent to wash off probes in which only a portion of the probe hybridizes to the fixed material. Detection of the probe on the washed filter indicate complementary sequences. One having ordinary skill in the art, using the sequence information disclosed in U.S. Pat. No. 5,237,051 and F. J. Sauvage et al. 1991 *J. Biol. Chem.* 266:17912–17918 can design probes which are fully complementary to mRNA sequences but not genomic DNA sequences. Hybridization conditions can be routinely optimized to minimize background signal by non-fully complementary hybridization.

The present invention includes labelled oligonucleotide which are useful as probes for performing oligonucleotide hybridization. That is, they are fully complementary with mRNA sequences but not genomic sequences. For example, the mRNA sequence includes portions encoded by different exons. The labelled probes of the present invention are labelled with radiolabelled nucleotides or are otherwise detectable by readily available nonradioactive detection systems.

According to the invention, diagnostic kits can be assembled which are useful to practice oligonucleotide hybridization methods of the invention. Such diagnostic kits comprise a labelled oligonucleotide which encodes portions of ST receptor encoded by different exons. It is preferred that labelled probes of the oligonucleotide diagnostic kits according to the present invention are labelled with a radionucleotide. The oligonucleotide hybridization-based diagnostic kits according to the invention preferably comprise DNA samples that represent positive and negative controls. A positive control DNA sample is one that comprises, a nucleic acid molecule which has a nucleotide sequence that is fully complementary to the probes of the kit such that the probes will hybridize to the molecule under assay conditions. A negative control DNA sample is one that comprises at least one nucleic acid molecule, the nucleotide sequence of which is partially complementary to the sequences of the probe of the kit. Under assay conditions, the probe will not hybridize to the negative control DNA sample.

Oligonucleotide hybridization techniques are useful for detecting mRNA encoding ST receptor in homogenized tissue samples and cells in body fluid samples. It is contemplated that PCR on the plasma portion of a fluid sample could be used to detect mRNA encoding ST receptor protein.

Tissue Analysis

Another aspect of the invention relates to methods of analyzing tissue samples which are fixed sections routinely prepared by surgical pathologists to characterize and evaluate cells. In some embodiments, the cells are from laminapropria and are analyzed to determine and evaluate the extent of metastasis of colorectal tumor cells. The laminapropria represents the barrier between the colorectal track and the rest of the body. By identifying the presence of ST receptor or mRNA that encodes ST receptor protein in cells of the laminapropria, the extent of invasion/infiltration of colorectal tumor cells into non-colorectal tissue can be evaluated. In some embodiments, the cells are removed in a biopsy or as an adenocarcinoma of unknown origin and are analyzed to determine and evaluate the whether they are colorectal tumor cells.

The present invention relates to in vitro kits for evaluating tissues samples to determine the level of metastasis and to reagents and compositions useful to practice the same. In some embodiments of the invention, tissue samples that include portions of the laminapropria may be isolated from individuals undergoing or recovery from surgery to remove colorectal tumors include resection or colonoscopy. The tissue is analyzed to identify the presence or absence of the ST receptor protein. Techniques such as an ST receptor/ligand binding assays and immunohistochemistry assays may be performed to determine whether the ST receptor is present in cells in the tissue sample which are indicative of metastatic migration. Alternatively, in some embodiments of the invention, tissue samples are analyzed to identify whether ST receptor protein is being expressed in cells in the tissue sample which indicate metastatic migration by detecting the presence or absence of mRNA that encodes the ST receptor protein. The presence of mRNA that encodes the ST receptor protein or cDNA generated therefrom can be determined using techniques such as in situ hybridization, immunohistochemistry and in situ ST binding assay.

The present invention relates to in vitro kits for evaluating samples of tumors to determine whether or not they are colorectal in origin and to reagents and compositions useful to practice the same. In some embodiments of the invention, tumor samples may be isolated from individuals undergoing or recovery from surgery to remove tumors in the colon, tumors in other organs or biopsy material. The tumor sample is analyzed to identify the presence or absence of the ST receptor protein. Techniques such as an ST receptor/ligand binding assays and immunohistochemistry assays may be performed to determine whether the ST receptor is present in cells in the tumor sample which are indicative of colorectal origin. Alternatively, in some embodiments of the invention, lumen tissue samples are analyzed to identify whether ST receptor protein is being expressed in cells in the tumor sample which indicate colorectal origin by detecting the presence or absence of mRNA that encodes the ST receptor protein. The presence of mRNA that encodes the ST receptor protein or cDNA generated therefrom can be determined using techniques such as in situ hybridization, immunohistochemistry and in situ ST binding assay.

In situ hybridization technology is well known by those having ordinary skill in the art. Briefly, cells are fixed and detectable probes which contain a specific nucleotide sequence are added to the fixed cells. If the cells contain complementary nucleotide sequences, the probes, which can be detected, will hybridize to them. One having ordinary skill in the art, using the sequence information in U.S. Pat. No. 5,237,051 and F. J. Sauvage et al. 1991 *J. Biol. Chem.* 266:17912–17918 can design probes useful in in situ hybridization technology to identify cells that express ST receptor.

The probes a fully complementary and do not hybridize well to partially complementary sequences. For in situ hybridization according to the invention, it is preferred that the probes are detectable by fluorescence. A common procedure is to label probe with biotin-modified nucleotide and then detect with fluorescently tagged avidin. Hence, probe does not itself have to be labelled with florescent but can be subsequently detected with florescent marker.

Cells are fixed and the probes are added to the genetic material. Probes will hybridize to the complementary nucleic acid sequences present in the sample. Using a fluorescent microscope, the probes can be visualized by their fluorescent markers.

According to the invention, diagnostic kits can be assembled which are useful to practice in situ hybridization methods of the invention are fully complementary with mRNA sequences but not genomic sequences. For example, the mRNA sequence includes portions encoded by different exons. It is preferred that labelled probes of the in situ diagnostic kits according to the present invention are labelled with a fluorescent marker.

Those having ordinary skill in the art can analyze the fixed cells to characterize the level of metastatic migration of the colon cancer cells. The labelling of colon-derived cells allows for improved analysis.

Immunohistochemistry techniques may be used to identify and essentially stain cells with ST receptor. Such "staining" allows for analysis of metastatic migration. Anti-ST receptor antibodies such as those described above of contacted with fixed cells and the ST receptor present in the cells reacts with the antibodies. The antibodies are detectably labelled or detected using labelled second antibody or protein A to stain the cells.

ST binding assays may be performed instead of immunohistochemistry except that the cell section is first frozen, then the ST binding assay is performed and then the cells are fixed.

The techniques described herein for evaluating tumor sections can also be used to analyze tissue sections for samples of lymph nodes as well as other tissues to identify the presence of colorectal tumor cells. The samples can be repared and "stained" to detect expression of ST receptor.

What is claimed is:

1. An in situ method of detecting invasion of neoplastic colorectal cells into the basement membrane of the laminapropria of a human comprising the steps of:

a) obtaining a sample of intestinal tissue which includes the basement membrane of the laminapropria;

b) contacting said sample with fully-complementary, detectable oligonucleotide probes that hybridize to mRNA that encodes ST receptor protein for a time sufficient for said fully-complementary, detectable oligonucleotide probes to hybridize to mRNA that encodes ST receptor protein present in cells of said sample;

c) removing detectable oligonucleotide probes which are not hybridized to mRNA that encodes ST receptor protein in cells of said sample; and d) examining said sample to detect the presence of detectable oligonucleotide probes hybridized to mRNA that encodes ST receptor protein present in cells in the basement membrane of the laminapropria;

wherein the presence of mRNA that encodes ST receptor protein in cells in the basement membrane of the laminapropria indicates invasion of neoplastic colorectal cells into the basement membrane of the laminapropria of an individual.

2. The method of claim 1 wherein said detectable oligonucleotide probe is labeled with a fluorescent marker.

3. An in situ method of detecting invasion of neoplastic colorectal cells into the basement membrane of the laminapropria of a human comprising the steps of:

a) contacting a sample of intestinal tissue which includes the basement membrane of the laminapropria with fully-complementary, detectable oligonucleotide probes that hybridize to mRNA that encodes ST receptor protein for a time sufficient for said fully-complementary, detectable oligonucleotide probes to hybridize to mRNA that encodes ST receptor protein present in cells of said sample;

b) removing detectable oligonucleotide probes which are not hybridized to mRNA that encodes ST receptor protein in cells of said sample; and c) examining said sample to detect the presence of detectable oligonucleotide probes hybridized to mRNA that encodes ST receptor protein present in cells in the basement membrane of the laminapropria;

wherein the presence of mRNA that encodes ST receptor protein in cells in the basement membrane of the laminapropria indicates invasion of neoplastic colorectal cells into the basement membrane of the laminapropria of an individual.

4. The method of claim 3 wherein said detectable oligonucleotide probe is labeled with a fluorescent marker.

* * * * *